United States Patent
Alexander et al.

(10) Patent No.: US 7,448,382 B1
(45) Date of Patent: Nov. 11, 2008

(54) PRESSURE SUPPORT SYSTEM WITH ACTIVE NOISE CANCELLATION

(75) Inventors: Paul Alexander, Plum, PA (US);
Chirstopher Habura, Manor, PA (US);
Patrick W Truitt, Murrysville, PA (US);
William A Truschel, Oakmont, PA (US)

(73) Assignee: RIC Investments, LLC, Wilmington, DE (US)

( * ) Notice: Subject to any disclaimer, the term of this patent is extended or adjusted under 35 U.S.C. 154(b) by 866 days.

(21) Appl. No.: 10/705,534

(22) Filed: Nov. 10, 2003

Related U.S. Application Data

(60) Provisional application No. 60/425,638, filed on Nov. 12, 2002.

(51) Int. Cl.
*A61M 16/00* (2006.01)

(52) U.S. Cl. .............. 128/204.18; 128/204.23; 381/71.3

(58) Field of Classification Search .......... 128/204.18, 128/203.13, 901, 200.24, 204.23, 204.26, 128/204.21; 381/71.1, 71.3, 71.5, 71.8, 71.12
See application file for complete search history.

(56) References Cited

U.S. PATENT DOCUMENTS

| | | | |
|---|---|---|---|
| 3,936,606 A | 2/1976 | Wanke | |
| 4,815,139 A | 3/1989 | Eriksson et al. | |
| 5,060,271 A | 10/1991 | Geddes | |
| 5,159,641 A | 10/1992 | Sopko et al. | |
| 5,283,834 A | 2/1994 | Goodman et al. | |
| 5,313,945 A | 5/1994 | Friedlander | |
| 5,816,242 A * | 10/1998 | Cewers | 128/204.21 |
| 6,058,932 A | 5/2000 | Hughes | |
| 6,398,739 B1 * | 6/2002 | Sullivan et al. | 600/529 |
| 7,155,388 B2 * | 12/2006 | Kushner et al. | 704/233 |
| 2001/0009153 A1 * | 7/2001 | Pessala et al. | 128/204.23 |

* cited by examiner

*Primary Examiner*—Steven O Douglas
(74) *Attorney, Agent, or Firm*—Michael W. Haas

(57) ABSTRACT

A medical device, such as a respiratory treatment device, having an active acoustic noise cancellation system. In one embodiment, the noise minimizing system includes at least one detector detecting characteristics of acoustic noise of a blower assembly and at least one speaker creating a cancellation frequency in the form of acoustic waves that at least partially cancels acoustic waves generated by the blower assembly. In another embodiment, the noise minimizing system includes a mechanical vibration generating element that creates a cancellation frequency in the form of a mechanical vibration that at least partially cancels vibrations of the blower assembly. This is accomplished, for example, by dithering a flow control valve at a frequency corresponding to an operating frequency of the blower assembly. Each embodiment can be used alone or in combination.

32 Claims, 4 Drawing Sheets

PRESSURE SUPPORT SYSTEM WITH ACTIVE NOISE CANCELLATION

CROSS-REFERENCE TO RELATED APPLICATIONS

This application claims priority under 35 U.S.C. § 119(e) from provisional U.S. patent application No. 60/425,638 filed Nov. 12, 2002, the contents of which are incorporated herein by reference.

BACKGROUND OF THE INVENTION

1. Field of the Invention

The present invention relates a method and apparatus for acoustic noise cancellation in medical devices and, more particularly, to respiratory treatment devices with acoustic noise cancellation.

2. Background Information

In the field of respiratory treatment devices, minimizing sound emission of the device is of significant concern. This is because respiratory treatment devices, such as a continuous positive airway pressure (CPAP) device, are commonly utilized by patients during periods of sleep, for example to treat sleep apnea. Any noise can serve to disrupt the patients sleep and should be minimized. In addressing this issue, existing respiratory devices have utilized sound insulating materials, e.g. foam, in the housing construction. The insulation or foams of the prior art are reliable methods of reducing airborne noise. However, achieving a sufficient noise reduction using sound insulating materials becomes difficult with smaller product profiles. In other words, as the respiratory treatment products are becoming smaller, the thickness of the insulation is decreased, and the effectiveness of the foam is reduced.

SUMMARY OF THE INVENTION

Accordingly, it is an object of the present invention to address the problem of noise reduction in respiratory treatment devices. It is a further object to provide an apparatus and method for noise reduction that is applicable to a variety of medical devices.

These objects are achieved by providing a medical device having acoustic noise cancellation. Specifically, the invention provides a respiratory treatment device in the form of an apparatus for delivering a flow of gas to the airway of a patient with acoustic noise cancellation. The apparatus includes a housing with a pressure generating system, such as a blower assembly, mounted in the housing. The blower assembly generates a flow of gas in a flow path within the housing. A patient circuit is coupled to the flow path of the housing and to the patient for communicating with and providing pressurized gas to the airway of a patient. The apparatus of the invention includes a system in the housing for minimizing acoustic noise of the blower assembly.

In one embodiment of the present invention, the acoustic noise minimizing system includes at least one detector detecting characteristics of acoustic noise of the blower assembly and at least one speaker creating a cancellation frequency in the form of acoustic waves that at least partially cancel acoustic waves generated by the blower assembly. Thus, the acoustic noise perceived by a person located a distance from the respiratory treatment device is minimized.

In a second embodiment of the present invention, a mechanical vibration inducing element is provided to create a cancellation frequency in the form of a mechanical vibration in at least a portion of the medical device. The mechanically induced vibration at the cancellation frequency at least partially cancels vibrations generated in the medical device due to operation of that device. For example, the present invention contemplates providing a valve operatively coupled to a pressure generator, such as the blower assembly, in the pressure generating system that is otherwise primarily used to control the pressure/flow of gas output by the pressure generating system to the airway of the patient and is operated under the control of a controller. In this embodiment, however, the valve also serves as the mechanical vibration inducing element in the acoustic noise minimizing system.

This is accomplished by actuating the valve so that the valve vibrates or dithers at a selected frequency based on the control signal provided to the valve by the controller. The dither frequency corresponds to the cancellation frequency and is selected to correspond to a frequency that matches the operating frequency of the pressure generator, so that the valve dither frequency effectively cancels out the blower vibrations that are otherwise perceived as noise. Thus, the valve acts as the mechanical vibration inducing element that creates the noise cancellation frequency.

The invention is not limited solely to respiratory devices but is applicable more broadly to medical devices. The invention, more broadly, is a system for reducing acoustic noise of a medical device having a housing and a noise source mounted in the housing. The system, in one embodiment, includes at least one detector within the housing detecting characteristics of acoustic noise of the noise source and at least one speaker within the housing creating acoustic waves that at least partially cancel acoustic waves generated by the noise source.

Additionally, the invention provides a method for reducing acoustic noise of a medical device having a housing and a noise source mounted in the housing. The method, in one embodiment, comprises the steps of detecting, within the housing, characteristics of acoustic noise of the noise source, and creating cancellation acoustic waves, within the housing, that at least partially cancel acoustic waves generated by the noise source, so that anyone near the noise source experiences a minimal amount of noise from the noise source. The method may further include the steps of generating a control signal for creating the cancellation acoustic waves, inverting the control signal, and increasing the magnitude of the control signal.

Further, the method is well suited for delivering pressurized gas to the airway of a patient, including the steps of generating a flow of gas for the patient and delivering the pressurized gas from the source of the pressurized gas to the airway of a patient. In this method, the minimizing acoustic noise is minimizing the noise associated with the generation of flow of the pressurized gas, wherein acoustic noise minimizing includes creating a cancellation frequency in the form of acoustic waves that at least partially cancel acoustic waves generated by the source of the pressurized gas. In a further method, which can be used alone or in combination with the previous method, a valve is provided to control the flow of gas delivered to such a patient. Minimizing acoustic noise is accomplished by providing creating a cancellation frequency in the form of mechanical vibrations, for example, by dithering the valve at a selected dither frequency, as the cancellation frequency that matches an operating frequency of the pressure generator.

In one embodiment of the invention, the apparatus that is used to detect characteristics of acoustic noise of the noise source is at least one microphone that generates a control signal for at least one speaker creating the cancellation acoustic waves. Further, the acoustic noise minimizing system may include at least one signal inverter inverting the control signal from each microphone. The apparatus may provide that each speaker creating the cancellation acoustic waves is directly driven by the inverted control signal from one signal inverter. Additionally, each signal inverter may be an amplifier that increases the magnitude of the control signal from the at least one microphone as well as inverting the control signal.

Further, in the respiratory device of the present invention, the microphone of the acoustic noise minimizing system may be an element of another system of the respiratory device, such as a snore detection system, an apnea detection system, a breathing disorder detection system, a compliance detection system, a patient detection system, a voice recognition control system, a system for conveying audible sounds to the user, a breathing pattern detection system, a patient monitoring system, a diagnostic system, an auto-titration system, or other known systems in which a microphone may be employed.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
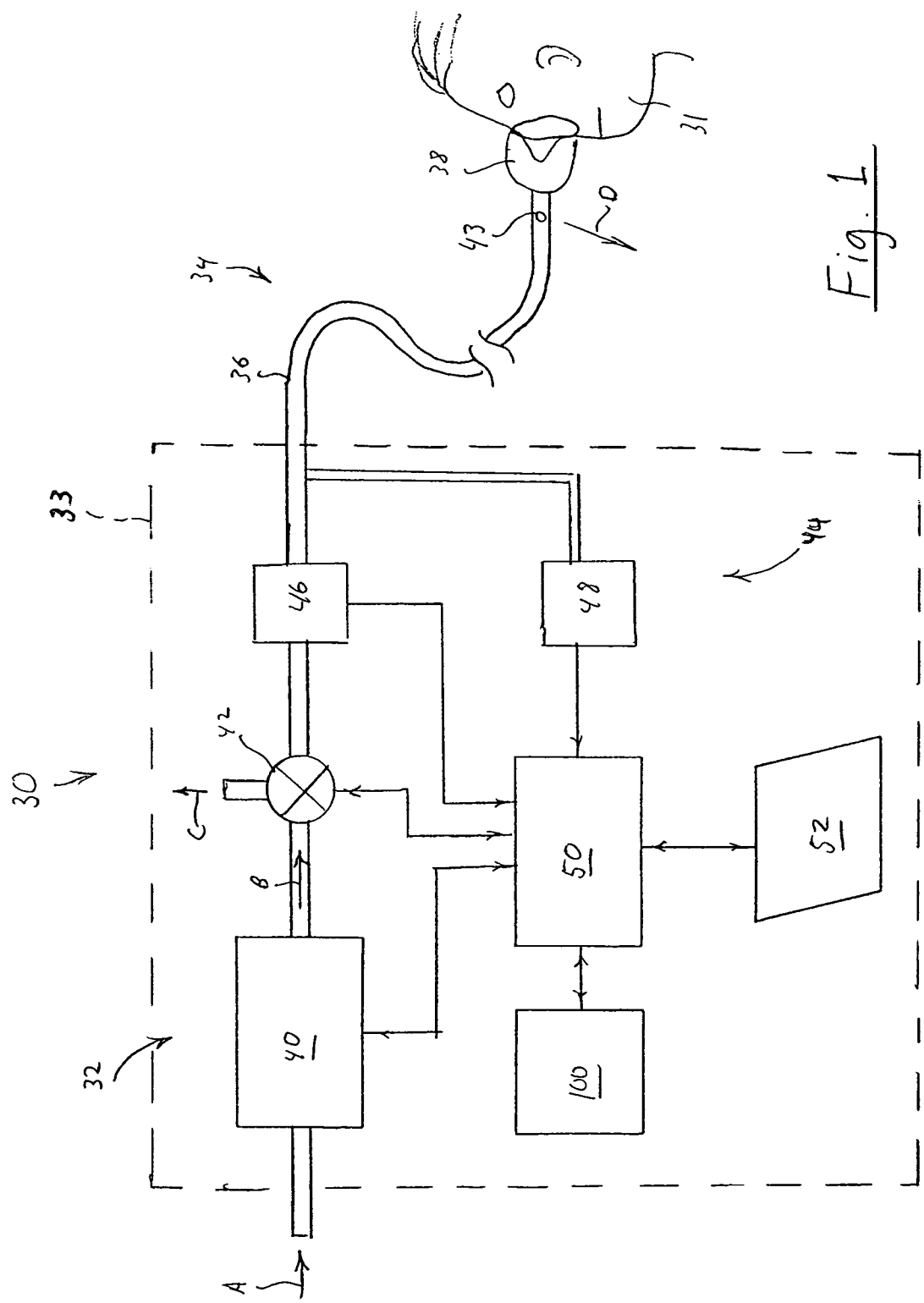
FIG. 1 is a schematic illustration of a respiratory treatment device including acoustic noise cancellation according to the principles of the present invention.
Figure 2:
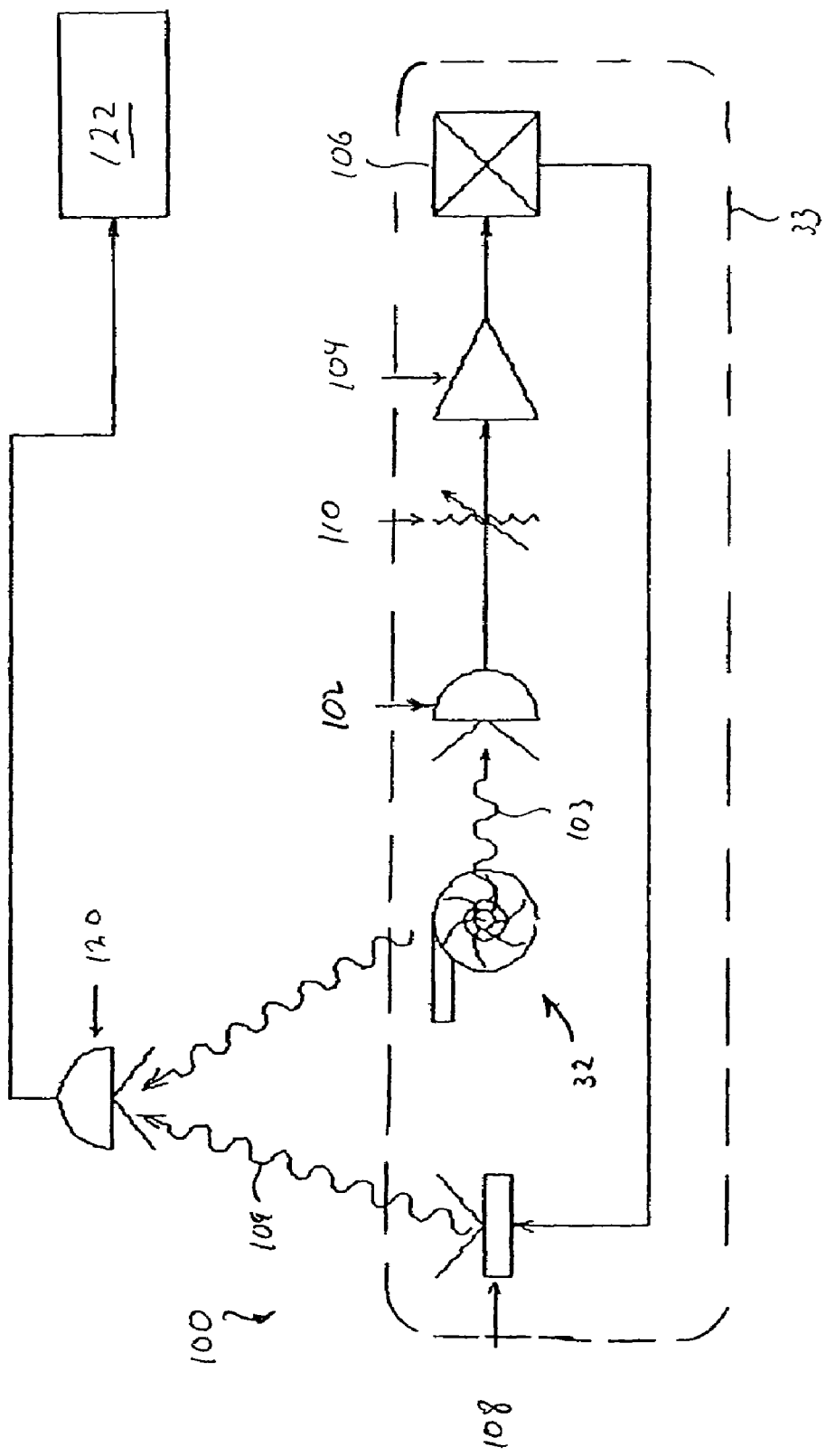
FIG. 2 is a schematic illustration of the acoustic noise cancellation system of the device of FIG. 1, and a schematic illustration of the testing setup for the device according to the present invention.

The present invention is schematically illustrated in FIGS. 1 and 2. A pressure support system 30 is generally for delivering pressurized gas to the airway of a patient 31. The present invention contemplates that pressure support system 30 is any pressure support system, such as a CPAP device, a bilevel device that delivers different pressure during inspiration and expiration, an auto-titration device that varies the pressure based on the monitored condition of the patient or the pressure support system, or the like as known in the art for delivering a pressurized breathing gas to an airway of a patient.

Pressure support system 30 includes a pressure generating system, generally indicated at 32, and a patient circuit 34, which includes a conduit 36 and a patient interface device 38. In the illustrated embodiment, pressure generating system 32 includes a pressure generator 40 and a pressure/flow control valve 42 as the outlet of the pressure generator.

Pressure generator 40 receives the breathing gas from a source of breathing gas, as indicated by arrow A, and outputs the breathing gas, as indicated by arrow B, to patient circuit 34 at a pressure that is greater than atmosphere for delivery to the airway of a patient (not shown). In a preferred embodiment of the present invention, pressure generator 40 is a mechanical pressure generator, such as a blower, bellows, or piston, that receives ambient air, for example, at an inlet from the gas source. Pressure control valve 42 controls the pressure of the flow of breathing gas delivered to the patient via the patient circuit by restricting the flow to the patient, by diverting flow from patient circuit 34, as indicated by arrow C, or a combination thereof.

The present invention further contemplates controlling the pressure of the flow of breathing gas delivered to the patient by controlling the operating speed of pressure generator 40, either alone or in combination with valve 42. Of course, valve 42 can be eliminated if operating speed alone is used to control the pressure of the flow of breathing gas delivered to the patient. Those skilled in the art can appreciate that other techniques for controlling the pressure of the flow of breathing gas delivered to the patient can be implemented in pressure support system 30, either alone or in combination to those discussed above. For example, a flow restricting valve (not shown) can be provided upstream of pressure generator 40 that controls the flow (arrow A) of gas to pressure generator 40, and, hence, the pressure of the flow of gas output for delivery to the patient.

Typically, the source of breathing gas is the ambient atmosphere, where its pressure is subsequently elevated for delivery to the patient by the pressure generating system. It is to be understood, that other sources of breathing gas, are contemplated by the present invention, such as oxygen or an oxygen mixture from an oxygen source. It is to be further understood, that the present invention contemplates that pressurized air can be provided to the airway of the patient directly from a tank of pressurized air via the patient circuit without using a pressure generator, such as a blower, bellows or piston, to increase the pressure of the air. Of course, a pressure regulator, such as valve 42, would be required to control the pressure of the gas delivered to the patient. The important feature with respect to the present invention is that pressurized breathing gas is provided in the patient circuit for delivery to the patient, not necessarily the source or manner in which the pressurized breathing gas is generated.

Although not shown in FIG. 1, the present invention also contemplates providing a secondary flow of gas, either alone or in combination with the primary flow of gas (arrow A) from atmosphere. For example, a flow of oxygen from any suitable source, such as an oxygen concentrator or oxygen storage device, can be provided upstream to pressure generator 40 or downstream of the pressure generator in the patient circuit or at the patient interface device to control the fraction of inspired oxygen delivered to the patient.

In the illustrated embodiment, conduit 36 in patient circuit 34 has one end coupled to the output of the pressure generator 40 and another end coupled to patient interface device 38. Conduit 36 is any tubing capable of carrying the gas flow from the pressure generator to the airway of the patient. Typically, a distal portion of the conduit 36 relative to pressure generator 40 is flexible to allow for freedom of movement of the patient. It is to be understood that various components may be provided in or coupled to patient circuit 34. For example, a bacteria filter, pressure control valve, flow control valve, sensor, meter, pressure filter, humidifier and/or heater can be provided in or attached to the patient circuit. Likewise, other components, such as muffler and filters can be provided at the inlet of pressure generator 40 and at the outlet of valve 42.

Patient interface device 38 in patient circuit 34 is any device suitable for communicating an end of conduit 36 with the airway of the patient. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive.

In the single limb patient circuit of the present invention, exhaled gas from the patient typically exits the patient circuit via an exhaust vent 43, as indicated by arrow D. In the illustrated embodiment, exhaust vent 43 is provided on a distal portion of conduit 34. Depending on the tidal volume of the patient and the pressure delivered by pressure support system 30, a small percentage of the exhaled gas may travel back up the conduit into pressure support system 30 and may even be exhausted to atmosphere through the gas inlet of the pressure generator and/or through a pressure/flow control valve 42, if such a valve is being used with the pressure generator.

Typically, exhaust vent 43 is an orifice provided in the conduit that communicates the interior of the conduit with atmosphere, with no active control over the flow of gas from the system. It is to be understood, however, that a wide variety of exhaust devices and configurations are contemplated for use with the pressure generating system of the present invention. For example, U.S. Pat. No. 5,685,296 to Zdrojkowski et al. discloses an exhalation device and method where the exhalation flow rate through the device remains substantially constant over a range of pressures in the patient circuit. This exhalation device, which is commonly referred to as a plateau exhalation valve or PEV, is suitable for use with the pressure support system of the present invention.

As shown in FIG. 1, pressure support system 30 includes a monitoring system, generally indicated at 44, to monitor the flow and pressure of gas delivered to the patient. In the illustrated embodiment, monitoring system 44 includes a flow sensor 46 that measures a rate at which the breathing gas flows within patient circuit 34. The present invention contemplates that any suitable sensor, such as a conventional pneumatach, can be used for flow sensor 46. It is to be further understood that flow sensor 46 need not be coupled directly to conduit 36. On the contrary, the present invention contemplates the use of any sensor or a plurality of sensors that can quantitatively measure airflow in the patient circuit. For example, flow in the system can be measured at the patient interface device or can be measured or estimated from the motor or piston speed or from torque used to provide the elevated pressure by pressure generator 40. In short, the present invention contemplates any conventional technique for measuring the flow of gas delivered to the patient.

Monitoring system 44 also includes a pressure sensor 48 that detects the pressure of the gas at the patient. In the illustrated embodiment, pressure sensor 48 is in fluid communication with patient interface device 38 via a conduit 36. In this embodiment, the pressure at the patient is estimated based on the known pressure drop that occurs in tubing 36. It is to be understood, however, that the patient pressure can be measured directly at patient interface device 38.

Pressure support system 30 includes a controller 50, which is preferably a microprocessor capable of implementing a stored algorithm, that receives the monitored variables, typically from flow sensor 46 and pressure sensor 48, and controls pressure generating system 32 based on these signals. Of course, controller 50 includes the necessary memory and processing capability to implement the features of the present invention.

The present invention further contemplates that pressure support system 30 includes an input/output interface 52 for communicating, information, data and/or instructions and any other communicatable items, collectively referred to as "data", between a user and controller 50. Examples of common input/output interfaces suitable for this purpose include a keypad and display. Other communication techniques, either hard-wired or wireless, are also contemplated by the present invention. For example, the present invention contemplates providing a smart card terminal that enables data to be loaded into controller 50 from the smart card or loaded onto the smart card from the controller. Other exemplary, interface devices and techniques adapted for use with the pressure support system include, but are not limited to, an RS-232 port, CD reader/writer, DVD reader/writer, RF link, modem (telephone, cable or other). In short, any conventional technique for providing, receiving, or exchanging data with controller are contemplated by the present invention as input/output device 52

Controller 50 also performs conventional leak estimation and respiratory cycle monitoring techniques. The present invention contemplates using any conventional technique for calculating leak $Q_{leak}$, which is the leakage of gas from the pressure support system and includes intentional leaks from the exhaust vent and unintentional leaks from the mask-patient interface, for example. The present invention also contemplates using any conventional technique for taking leak into consideration when determining the patient flow $Q_{patient}$, which is the flow of gas at the airway of the patient, and total flow $Q_{total}$, which is the flow of gas typically measured by flow sensor 46. For example, U.S. Pat. Nos. 5,148,802 to Sanders et al., 5,313,937 to Zdrojkowski et al., 5,433,193 to Sanders et al., 5,632,269 to Zdrojkowski et al., 5,803,065 to Zdrojkowski et al., 6,029,664 to Zdrojkowski et al., 6,360,741 to Truschel, 6,920,875 to Frank et al., and 6,626,175 to Jafari et al., the contents of each of which are incorporated by reference into the present invention, all teach techniques for detecting and estimating leak and managing the delivery of breathing gas to the patient in the presence of leaks.

The present invention also contemplates using any conventional technique for detecting the inspiratory and expiratory phases of the patient's respiratory cycle. For example, U.S. Pat. Nos. 5,148,802 to Sanders et al., 5,313,937 to Zdrojkowski et al., 5,433,193 to Sanders et al., 5,632,269 to Zdrojkowski et al., 5,803,065 to Zdrojkowski et al., 6,029,664 to Zdrojkowski et al., and 6,626,175 to Jafari et al., all teach techniques for differentiating between the inspiratory and expiratory phases of a respiratory cycle.

A key aspect of the present invention is the provision of a system 100 in housing 33 for minimizing acoustic noise associated with the operation of pressure support system 32. Housing 33 contains the above-described elements of the pressure support system, except for the portion of conduit 36 that is outside the housing and patient interface device 38. Acoustic noise minimizing system 100 according to a first embodiment of the present invention is shown in FIG. 2 and includes at least one detector, specifically a microphone 102, detecting characteristics of acoustic noise 103 from a noise source, such as pressure generating system 32. It is anticipated that other sensors could be utilized to detect other characteristics of the acoustic noise of the pressure generating system 32. However, microphone 102 may have other uses in a respiratory treatment device 10 as discussed below making it particularly well suited for detecting characteristics of acoustic noise from the noise source.

Microphone 102 generates an electrical control signal, the amplitude of which is increased by amplifier 104. Amplifier 104 also inverts the control signal, which is shown separately as a distinct phase reversal switch 106 in FIG. 2. The inverted, amplified control signal drives at least one loudspeaker 108 that creates a cancellation energy in the from of cancellation acoustic waves 109 that at least partially cancel acoustic waves generated by pressure generating system 32. As a result, a person located a distance from pressure support system 30 perceives little, if any, noise from the pressure support system. FIG. 2 additionally shows a variable attenuator 110 positioned prior to the amplifier 34 for controlling the output of the microphone 102.

Acoustic noise minimizing system 100 of the present invention operates on the principle of summing the sound or acoustic waves of an undesired sound source, i.e., pressure generating system 32, with those from a second source, i.e., loudspeaker 108, such that at least partial cancellation of the undesired sound waves occur. The noise source, e.g., pressure generating system 32, produces audible sound by producing pressure waves in the air surrounding the source. These pressure waves are converted into movement of the eardrum of the listener and are perceived as sound by the listener. Microphone 102 placed near the noise source and within housing 33 receives these pressure waves and converts them into the control signal, which is the output of the microphone 102. For example, microphone 102 produces a positive voltage in response to a high pressure and a negative voltage in response to a low pressure.

Other output control signals are, of course, possible. The control signal is amplified and inverted as described above to directly drive loudspeaker 108. Acoustic noise minimizing system 100 is arranged such that the sound pressures from loudspeaker 108 are in opposition to those from the noise source, i.e., pressure generating system 32. That is, when the noise source is producing a decreasing pressure wave, loudspeaker 108 is producing an increasing pressure wave, and vice versa. If the gain of amplifier 104 is adjusted such that the output of the sound pressure from loudspeaker 108 is equal to that of the noise source, but opposite in phase, cancellation of the sound pressures occurs at some point distant from the noise source.

Additionally, advantages may be gained through the use of multiple microphones 102 and speakers 108. Acoustic noise minimizing system 100 may be further improved through the use of filters, delay mechanisms to alter the phase and amplitude verses frequency response. The field of acoustic noise cancellation is well established. U.S. Pat. Nos. 3,936,606; 4,815,139; 5,060,271; 5,063,598; 5,283,834; and 5,313,945 describe several acoustic noise attenuation systems and these references are incorporated herein by reference. Advanced methods will likely result in better cancellation of the undesired noise.

Figure 3:
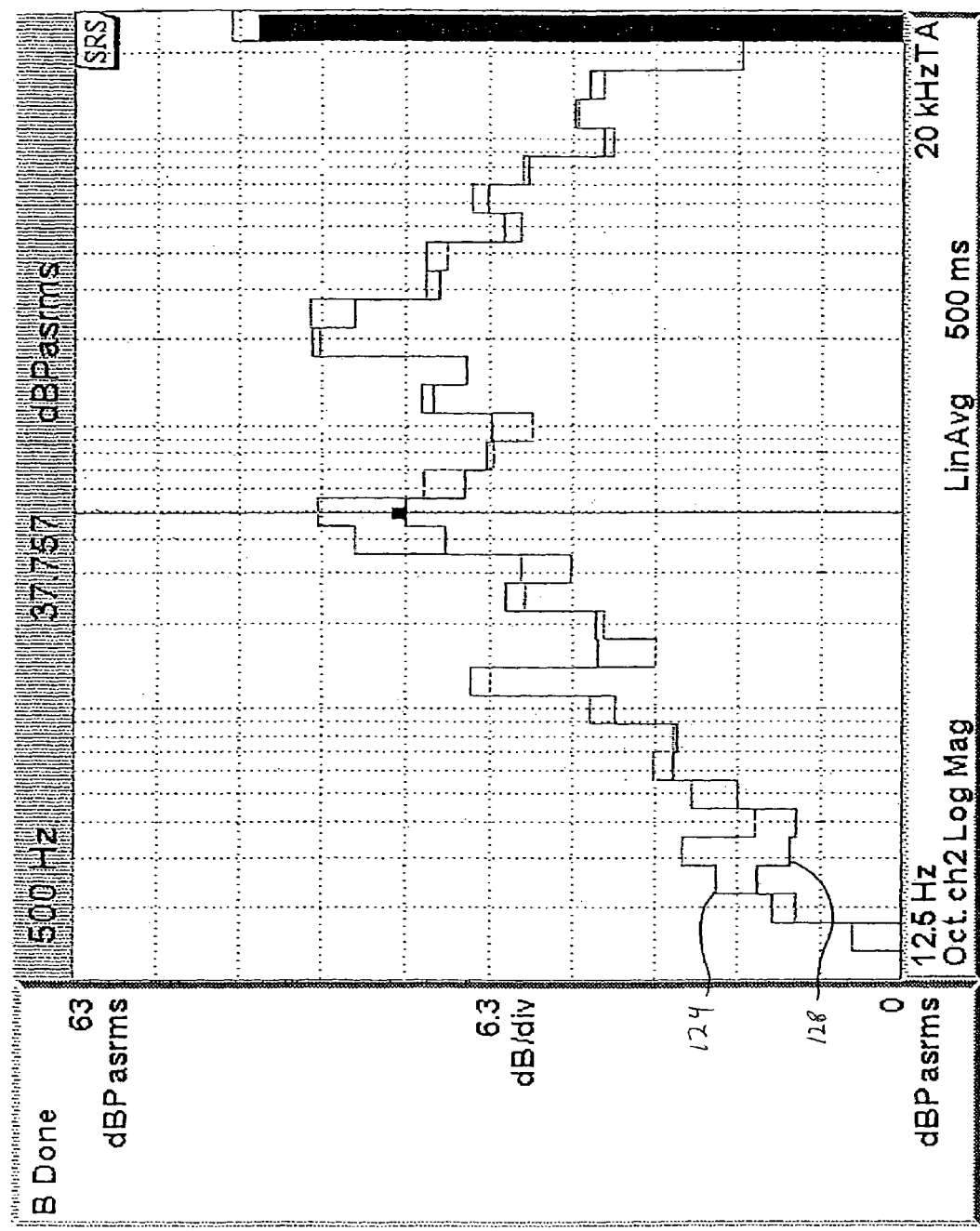
FIGS. 3 and 4 are plots of test results comparing the acoustic output of the respiratory treatment device of FIG. 1 with and without the acoustic noise cancellation system operating.
Figure 4:
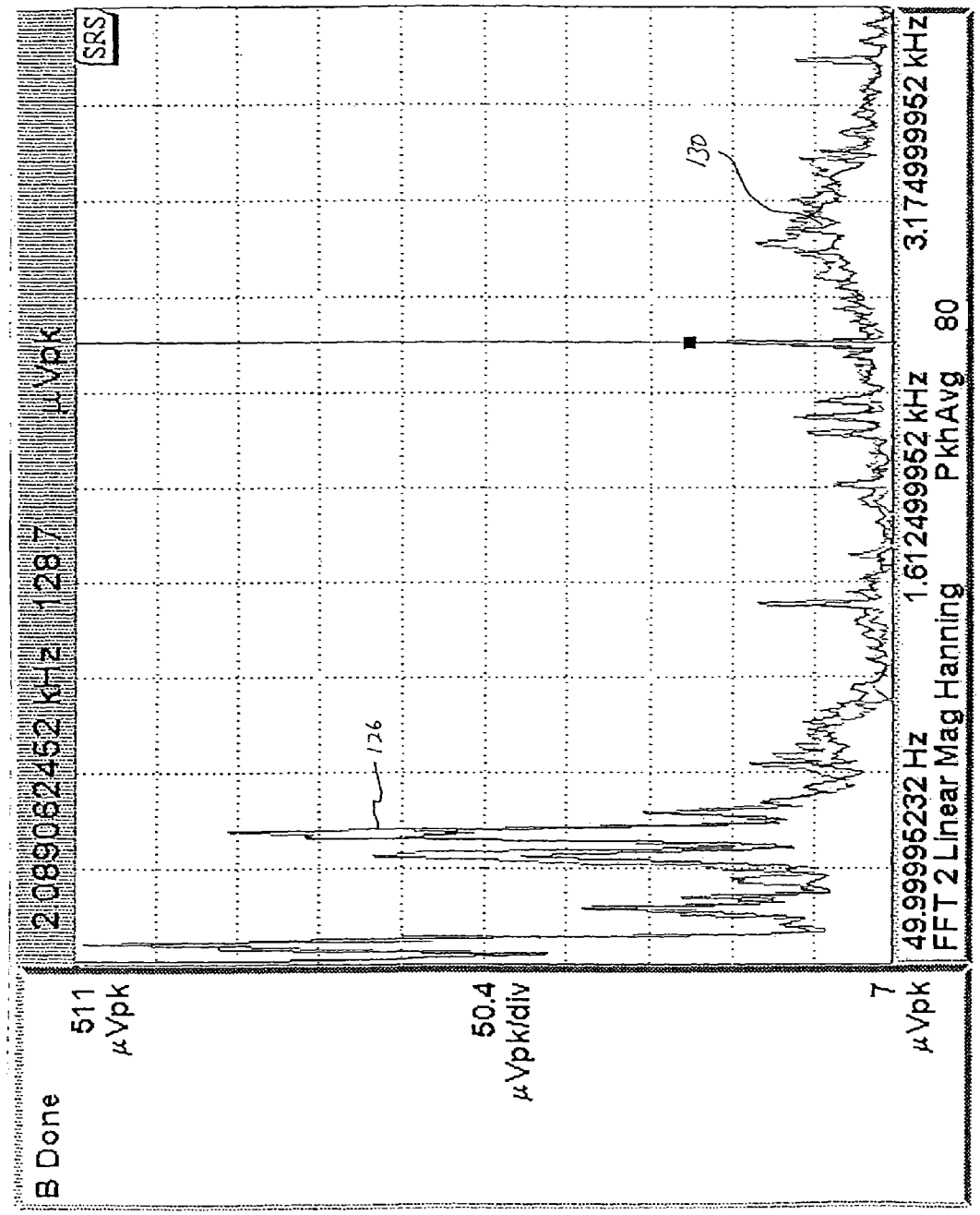

Pressure support system 30 was tested using an analyzer microphone 120 at a fixed distance from acoustic noise minimizing system 100 and coupled to an audio spectrum analyzer 122. The results are graphically shown in FIGS. 3-4. Lines 124 and 126 represent the results without acoustic noise minimizing system 100 operating, while lines 118 and 120 represent the results using acoustic noise minimizing system 100 of the present invention. The plots demonstrate that noise cancellation is occurring. For example, A 6 dB reduction is seen in the 500 Hz third octave band and an overall sound pressure reduction of 2 dB is observed with the use of acoustic noise minimizing system 100.

The present invention contemplates that acoustic noise minimizing system 100 can operate independently of the other components of the pressure support system. However, it is also contemplated that the processing elements can be provided in controller 50 with the microphone and speaker being the main hardware components of acoustic noise minimizing system 100. In addition, microphone 102 can be directed to detect noise from within housing 33, from outside the housing, or both. Similarly, speaker 108 can be directed to generate the cancellation acoustic waves 109 within housing 33 outside the housing, or both.

In the description of the present invention provided above, the noise source has been described as being the pressure generating system. It is to be understood, however, that the present invention contemplates that noise can come from other sources and is not intended to be limited to the cancellation of noise produced only by the pressure support system. For example, the operation of valve 42 and the movement of gas within the patient circuit, and the exhausting of gas therefrom can produce sounds that are capable of being actively cancelled by acoustic noise minimizing system 100.

The present invention further contemplates that microphone 102 of acoustic noise minimizing system 100 forms a portion of another system or component of the pressure support system 30. For example a snore detection system could also utilize the microphone 102. Other possibilities include an apnea detection system, a breathing disorder detection system, a compliance detection system, a patient detection system, a voice recognition control system, a system for conveying audible sounds to the user, a breathing pattern detection system, a patient monitoring system, a diagnostic system, an auto-titration system, or other known systems in which a microphone may be employed. These other systems already exist utilizing microphones and the details of which do not form key aspects of the present invention and are not described herein in detail. The important aspect is that microphone 102 can be incorporated as an integral component of several systems in addition to acoustic noise minimizing system 100 of the invention.

A second embodiment of the present invention contemplates producing a cancellation energy in the form of a mechanical vibration, by means of a mechanical vibration generating element, such that a cancellation mechanical vibration is created in at least a portion of a medical device. The mechanically induced cancellation vibration at least partially cancels mechanical vibrations generated in the medical device due to operation of that device. For example, the present invention contemplates making use a valve, e.g., pressure/flow control valve 42 in FIG. 1, that is otherwise used to control the pressure/flow delivered to the patient as a mechanical vibration generating element in an acoustic noise minimizing system. As noted above, valve 42 is primarily used to control the pressure/flow of gas output by the pressure generating system to the airway of the patient and is operated under the control of a controller. In this embodiment, the acoustic noise minimizing system includes actuating the valve so that the valve vibrates or dithers at a selected frequency. The frequency at which the valve dithers is preferably determined based on the control signal provided to the valve by the controller.

The dither frequency is specifically selected to correspond to a frequency that matches the operating frequency of pressure generator 40. In this manner, the valve dither frequency serves as a cancellation frequency that effectively cancels out the vibrations of the pressure generator, such as the blower, that are otherwise perceived as noise. If the pressure generator is driven at a constant speed, the dither frequency can also be fixed. However, the present invention contemplates varying the dither frequency if the operating frequency of the pressure generator varies.

The present invention contemplates that the pressure/flow control valve is any conventional valve, so long as it is capable of being dithered. However, a preferred embodiment for the pressure/flow control valve is the sleeve valve disclosed in U.S. Pat. No. 6,615,831, the contents of which are incorporated herein by reference. In this embodiment, dithering is accomplished by applying an alternating current to the valve coil at a cancellation frequency that is equal to the frequency of the motor shaft line, but out of phase. In one embodiment of the present invention, the dither signal is superimposed on the control signal to the coil and causes the valve to produce a structural vibration that is mechanically transmitted from the valve to the valve support housing. In this manner, manipulation of the dither (cancellation) frequency cancels out the structural vibration of the motor shaft frequency due to rotation of the motor shaft. The present invention also contemplates providing two signals to the coil—a control signal and a dither signal—to achieve the valve control and dither functions.

It should be understood that in this second embodiment, the mechanical cancellation frequency can be generated by elements other than the pressure/flow control valve. For example, the present invention contemplates providing a separate or dedicated vibration generating element, as known to those in the art, coupled to any desired component in the medical device where a cancellation frequency is to be generated. In addition, a feedback system can be used to determine the cancellation frequency for the vibration inducing element as in the first embodiment. It should also be understood that the mechanical vibration cancellation technique of this embodiment can be used alone or in combination with the noise cancellation technique discussed above.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An apparatus for delivering a flow of gas to the airway of a patient the apparatus comprising:
   (a) a housing;
   (b) gas flow generating means for providing disposed in the housing and adapted to generate a flow of a gas;
   (c) gas delivery means adapted to be coupled to the gas flow generating generator means and adapted to be coupled to a patient for communicating the flow of gas with an airway of such a patient; and
   (d) means for minimizing acoustic noise of the gas flow generating means by generating a cancellation frequency that at least partially cancels acoustic waves generated by the gas flow generating means, wherein the means for minimizing acoustic noise includes a speaker operatively coupled to the housing and adapted to create cancellation acoustic waves at a cancellation frequency, and wherein the speaker is operatively coupled to the housing so as to direct the cancellation acoustic waves into over an area outside the housing such that the cancellation frequency reduces acoustic noise resulting from operation of the gas flow generating means, the reduction of the acoustic noise being at a location outside the housing.

2. The apparatus of claim 1, wherein the means for minimizing acoustic noise includes a mechanical vibration generating means, operatively coupled to the apparatus, for creating cancellation mechanical vibrations as the cancellation frequency that at least partially cancels acoustic waves generated by the gas flow generating means.

3. The apparatus of claim 2, wherein the gas flow generating means includes a pressure generator and a valve, wherein the mechanical vibration generating means includes dithering means for causing the valve to oscillate at a selected dither frequency as the cancellation frequency, and wherein the dither frequency substantially corresponds to an operating frequency of the pressure generator.

4. The apparatus of claim 1, wherein the means for minimizing acoustic noise includes a microphone adapted to generate a control signal for creating the cancellation frequency.

5. The apparatus of claim 4, wherein the means for minimizing acoustic noise includes a signal inverter adapted to invert the control signal from each microphone.

6. The apparatus of claim 5, wherein the speaker is driven by an inverted control signal from the signal inverter.

7. The apparatus of claim 4, wherein the microphone is an element of at least one of the group consisting of: snore detection means, apnea detection means, breathing disorder detection means, compliance detection means, patient detection means, voice recognition control means, means for conveying audible sounds to the user, breathing pattern detection means, patient monitoring means, diagnostic means, and auto-titration means.

8. An apparatus for delivering a flow of gas to an airway of a patient, the apparatus comprising:
   (a) a housing;
   (b) a blower assembly mounted in the housing, the blower assembly adapted to generate a flow of gas;
   (c) a gas delivery circuit coupled to an outlet of the blower assembly and adapted to communicate the flow of gas with an airway of such a patient; and
   (d) a cancellation energy generating system adapted to create a cancellation energy that at least partially cancels acoustic waves generated by the blower assembly, wherein the cancellation energy generator is a speaker operatively coupled to the housing and adapted to create cancellation acoustic waves as the cancellation energy, and wherein the speaker is disposed so as to direct the cancellation acoustic waves into over an area outside the housing such that the cancellation frequency reduces acoustic noise at a location outside the housing, the acoustic noise being noise associated with operation of the blower assembly.

9. The apparatus of claim 8, wherein the cancellation energy generator is a mechanical vibration generating element operatively coupled to the blower assembly and adapted to create cancellation mechanical vibrations as the cancellation energy that at least partially cancels acoustic waves generated by the blower assembly.

10. The apparatus of claim 9, wherein the blower assembly includes a pressure generator, a valve in fluid communication with the pressure generator, and a controller operatively coupled to the valve to control actuation of the valve, wherein the controller causes the valve to oscillate at a selected dither frequency that substantially corresponds to an operating frequency of the pressure generator, such that the valve defines the mechanical vibration generating element.

11. The apparatus of claim 8, further comprising a detector adapted to detect a characteristic of acoustic noise of the blower assembly, and wherein the cancellation energy generating system creates the cancellation energy based on an output of the detector.

12. The apparatus of claim 11, wherein the detector is a microphone adapted to generate a control signal for creating the cancellation energy.

13. The apparatus of claim 12, wherein the microphone is an element of at least one of the group consisting of: snore detection means, apnea detection means, breathing disorder detection means, compliance detection means, patient detection means, voice recognition control means, means for conveying audible sounds to the user, breathing pattern detection means, patient monitoring means, diagnostic means, and auto-titration means.

14. A system for reducing acoustic noise of a medical device having a housing and a noise source including a gas flow generating means mounted in the housing, the system comprising:
   a detector disposed within the housing adapted to detect a characteristic of acoustic noise of the noise source; and
   a cancellation energy generator disposed within the housing adapted to create a cancellation energy that at least partially cancels acoustic waves generated by the noise source, wherein the cancellation energy generator includes a speaker adapted to create cancellation acoustic waves as the cancellation energy, and wherein the speaker is disposed so as to direct the cancellation acoustic waves into over an area outside the housing such that the cancellation frequency reduces sound levels of the gas flow generating means at a location outside the housing.

15. The system of claim 14, wherein the cancellation energy generator is a mechanical vibration generating element adapted to create cancellation mechanical vibrations as the cancellation energy that at least partially cancels acoustic waves generated by the noise source.

16. The system of claim 14, wherein the detector includes a microphone adapted to generate a control signal for the cancellation energy generator.

17. The system of claim 16, further including a signal inverter adapted to invert the control signal from the microphone.

18. The system of claim 17, wherein the cancellation energy generator is driven by an inverted control signal from the signal inverter.

19. A method for delivering a flow of gas to the airway of a patient, the method comprising the steps of:
   (a) providing a gas flow generating system including a housing and a gas flow generator disposed in the housing;
   (b) generating a flow of gas via the gas flow generator;
   (c) delivering the flow of gas to an airway of a patient;
   (d) minimizing acoustic noise associated with generating the flow of the pressurized gas, delivering the flow of gas, or both, by creating a cancellation energy that at least partially cancels acoustic waves associated with generating the flow of gas, delivering the flow of gas, or both; and
   (e) emitting the cancellation energy over an area outside the housing such that the cancellation frequency reduces acoustic noise at a location outside the housing, the acoustic noise being noise associated with generating the flow of the pressurized gas, delivering the flow of gas, or both.

20. The method of claim 19, wherein emitting the cancellation energy over the area includes creating cancellation acoustic waves via a speaker as the cancellation energy.

21. The method of claim 19, wherein creating the cancellation energy includes creating cancellation mechanical vibrations as the cancellation energy that at least partially cancels the acoustic noise.

22. The method of claim 21, wherein creating cancellation mechanical vibrations includes causing a pressure/flow control valve to oscillate at a selected dither frequency that substantially corresponds to an operating frequency of the pressure generator that generates the flow of gas.

23. The method of claim 19, wherein minimizing the acoustic noise includes providing a microphone generating a control signal for creating the cancellation energy.

24. The method of claim 23, wherein the minimizing acoustic noise includes inverting the control signal from each microphone.

25. The method of claim 24, wherein the minimizing acoustic noise includes providing a speaker creating cancellation acoustic waves as the cancellation energy based on an inverted control signal from one the signal inverter.

26. The method of claim 23, wherein the microphone is an element of at least one of the group consisting of: snore detection means, apnea detection means, breathing disorder detection means, compliance detection means, patient detection means, voice recognition control means, means for conveying audible sounds to the user, breathing pattern detection means, patient monitoring means, diagnostic means, and auto-titration means.

27. The method of claim 19, further comprising providing a valve to control the flow of gas delivered to such a patient, and wherein minimizing acoustic noise includes dithering the valve at a selected dither frequency as the cancellation frequency that substantially matches an operating frequency of the pressure generator.

28. A method for reducing acoustic noise of a medical device having a housing and a noise source mounted in the housing, the method comprising the steps of:
   detecting, within the housing, characteristics of acoustic noise associated with the noise source wherein the acoustic noise is noise associated with at least one of generating a flow of gas, delivering a flow of gas, or both;
   creating a cancellation energy, within the housing, that at least partially cancel acoustic waves generated by the noise source; and
   emitting the cancellation energy over an area outside the housing such that the cancellation frequency energy reduces acoustic noise resulting from operation of the medical device.

29. The method of claim 28, wherein emitting the cancellation energy over the area includes creating cancellation acoustic waves via a speaker as the cancellation energy.

30. The method of claim 28, wherein creating the cancellation energy includes creating cancellation mechanical vibrations as the cancellation energy that at least partially cancels the acoustic noise.

31. The method of claim 30, wherein creating cancellation mechanical vibrations includes causing a pressure/flow control valve to oscillate at a selected dither frequency that substantially corresponds to an operating frequency of the pressure generator that generates the flow of gas.

32. The method of claim 28, further including the step of generating a control signal for creating the cancellation energy.

* * * * *